United States Patent [19]

Elist

[11] Patent Number: 5,445,594
[45] Date of Patent: Aug. 29, 1995

[54] IMPLANT FOR EXPANDING PENILE GIRTH AND LENGTH

[76] Inventor: James J. Elist, 9301 Wilshire Blvd., Suite 401, Beverly Hills, Calif. 90210

[21] Appl. No.: 223,045

[22] Filed: Apr. 5, 1994

[51] Int. Cl.⁶ ............................. A61F 2/26; A61F 5/00
[52] U.S. Cl. ........................................................ 600/38
[58] Field of Search .......................... 600/29, 30, 38–41

[56] References Cited

U.S. PATENT DOCUMENTS

| | | | |
|---|---|---|---|
| 4,204,530 | 5/1980 | Finney | 600/40 |
| 4,235,227 | 11/1980 | Yamanaka | 600/40 |
| 4,381,767 | 5/1983 | Finney | 128/79 |
| 4,387,705 | 6/1983 | Finney | 128/1 R |
| 4,523,584 | 6/1985 | Yachia et al. | 600/38 |
| 4,602,625 | 7/1986 | Yachia et al. | 600/40 |
| 4,665,903 | 5/1987 | Whitehead | 600/40 |
| 5,069,201 | 12/1991 | Zinner et al. | 600/40 |
| 5,101,813 | 4/1992 | Trick | 600/40 |

FOREIGN PATENT DOCUMENTS 835637 4/1952 Germany.

Primary Examiner—Lee S. Cohen
Assistant Examiner—Samuel Gilbert
Attorney, Agent, or Firm—Macro-Search Corp.; Gene Scott

[57] ABSTRACT

An implant device is disclosed for expanding the girth and length of a penis. A soft, flexible body is implanted between the shaft and the skin of the penis. The body takes the shape of a partial cylindrical sleeve that has an outer, relatively elastic sheet member and an inner, relatively inelastic sheet member. When implanted, the body covers the corpus cavernosum of the penis and does not or only partially covers the urethra, and extends in length between the glans penis and the base of the penis. A principally closed sack is formed between the inner and outer sheet members for receiving a fluid under pressure from a fluid source. Spring-like ribs are embedded within the inner sheet member for preventing collapse of the inner sheet member when the body is deflated.

14 Claims, 2 Drawing Sheets

IMPLANT FOR EXPANDING PENILE GIRTH AND LENGTH

FIELD OF THE INVENTION

This invention relates generally to inflatable penile implants and, more particularly, is directed towards an implant device for increasing penile girth and length.

BACKGROUND OF THE INVENTION

Penile implants for impotence in males are known in the prior art, and are taught, for example, in U.S. Pat. No. 4,602,625 to Yachia et al. on Jul. 29, 1986; U.S. Pat. No. 4,523,584 to Yachia et al. on Jun. 18, 1985; and U.S. Pat. No. 4,204,530 to Finney on May 27, 1980. Such devices are typically inflated when an erection is desired, and then subsequently deflated. During inflation, however, such devices tend to press inwardly on the corpora cavernosa in an uncomfortable fashion. Furthermore, such devices have inflation chambers that look and feel unnatural when inflated. For patients that have the availability to achieve a natural erection at least some of the time, such devices can cause severe discomfort if the device is not inflated at a rate corresponding to the natural erection.

Such prior art devices are aimed primarily at hose suffering impotence. As such, many such devices are not suitable for patients who do not suffer impotence but instead desire a more natural looking penis, either because of a deformity, injury, or naturally small penis size. These types of patients do not need a device for obtaining an erection. Instead, these patients need a device or method for augmenting penis size. To this end, a procedure of injecting autologous fat obtained by liposuction into the penis has been developed. However, such procedures can result in various complications such as oil cyst formation, infection, and transient edema and eccchymosis.

Clearly, then, there is a need for a penile implant device that is primarily directed at augmenting penis size as opposed to treating impotence. Such a needed device would be able to accommodate natural changes is penile length without causing discomfort. Such a needed device would not collapse when deflated, and when inflated would also not press inwardly on the shaft of the penis or otherwise comprise proper blood flow. Furthermore, such device would have a smooth, natural look and feel, while either flaccid or inflated. The present invention fulfills these needs and provides further related advantages.

SUMMARY OF THE INVENTION

The present invention is an implant device for expanding the girth and advancement or length of a penis. A soft, flexible body is implanted between the shaft and the skin of the penis. The body takes the shape of a partial cylindrical sleeve that has an outer, relatively elastic sheet member and an inner, relatively inelastic sheet member. When implanted, the body covers the corpus cavernosum of the penis and does not or only partially covers the urethra, and extends in length between the glans penis and the base of the penis. A principally closed sack is formed between the inner and outer sheet members for receiving a fluid from a fluid pressurization source. Spring-like ribs are embedded within the inner sheet member for preventing collapse of the inner sheet member when the body is deflated.

The present invention is a penile implant device that is primarily directed at increasing penile girth and length, and can accommodate natural changes is penile length without causing discomfort. As such, the present invention is well suited for patients that can achieve a natural erection, yet suffer from small penis size or from a penile malformity, for example. The present device does not press inwardly on the shaft of the penis when inflated, and further has a smooth, natural look and feel, when either flaccid or inflated. Other features and advantages of the present invention will become apparent from the following more detailed description, taken in conjunction with the accompanying drawings, which illustrate, by way of example, the principals of the invention.

DETAILED DESCRIPTION OF THE PREFERRED EMBODIMENT

Figure 1:
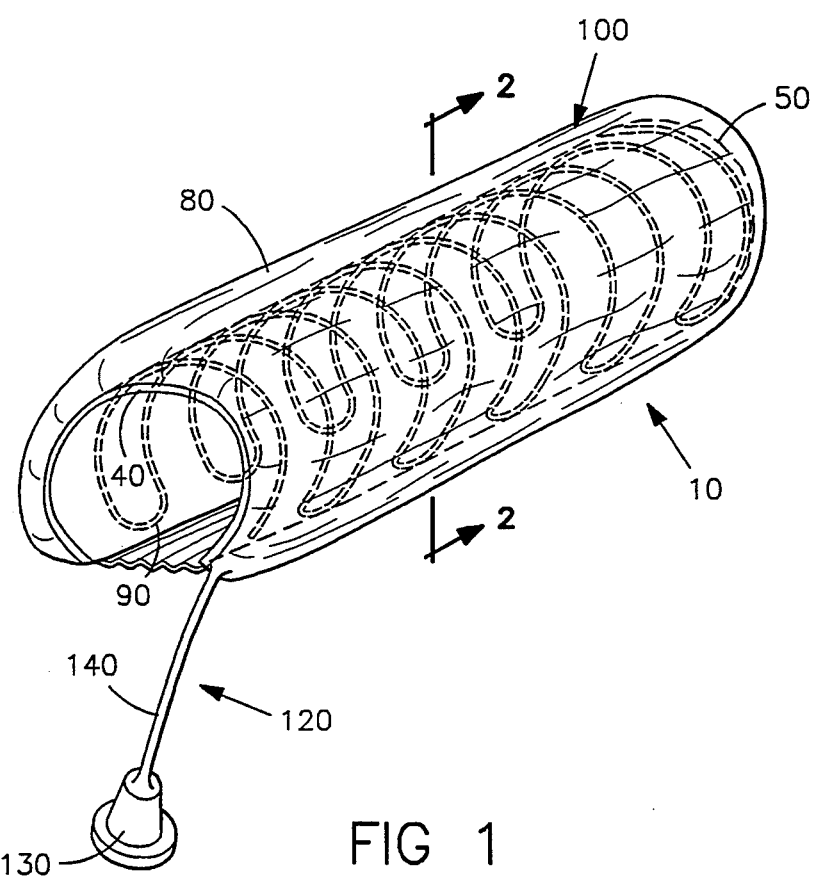
FIG. 1 is a perspective illustration of an implant device for expanding the girth and length of a penis, illustrating an outer elastic sheet member surrounding a relatively inelastic inner sheet member, together which form a partially cylindrical body.
Figure 2:
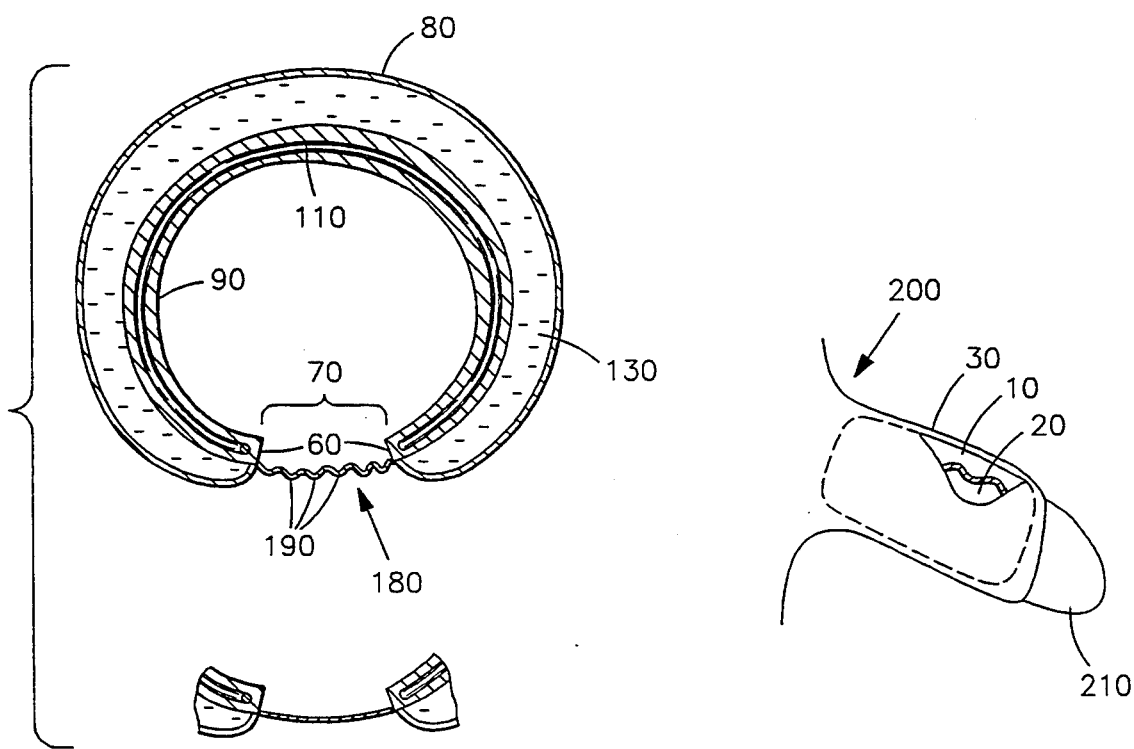
FIG. 2 is a cross-sectional view of the invention, taken generally along lines 2—2 of FIG. 1, illustrating a fan-folded elastic membrane bridging a gap formed between side edges of the inner and outer sheet members, and further illustrating spring-like ribs embedded within the inner sheet member.
Figure 3:
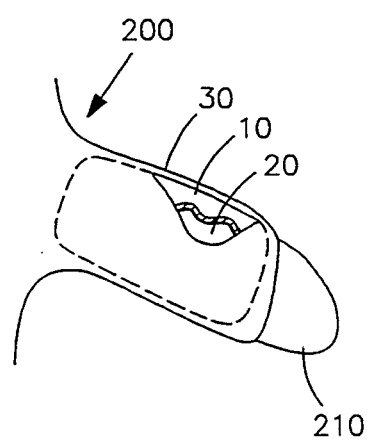
FIG. 3 is a right-side elevational view of the invention, partially broken away, illustrating the device as implanted in the penis.

FIGS. 1 and 2 show an implant device for expanding the girth and length of a penis. A soft, flexible body 10 is provided for implanting about a penile shaft 20 beneath the penile skin 30, that is, between the shaft 20 and the skin 30 of the penis. Surgical procedures for implanting such a device as well described in U.S. Pat. No. 4,204,530 to Finney on May 27, 1980, which is hereby incorporated into the present application by reference. The body 10 is formed into the shape of an elongated partial cylinder, with a first end edge 40 and a second end edge 50 defining the length of the body 10. Such length is preferably sufficient to extend from the glans penis 210 to the base of the penis 200, on average 100 millimeters. Two opposing side edges 60 are spaced apart from each other to define both the circumferential limits of the cylinder and a space 70 therebetween. The partial cylinder is preferably of a circumference sufficient to cover the corpus cavernosum of a penis without covering, or only partially covering, the urethra (FIG.

2). An outer, relatively elastic sheet member 80 of stretchable material is joined along the side and end edges 40,50,60 to an inner, relatively inelastic sheet member 90. As such, a principally closed sack 100 is formed. The sheet members 80,90 are formed from a physiologically acceptable, biologically inert material, such as silicone rubber, or the like. The inner sheet member 90 is preferably about 1.2 mm thick, and the outer sheet member 80 is preferably from 0.1 mm to 0.3 mm thick. Optionally, a second sheet member 80 may be included for protecting against leakage in the event that the first outer sheet member 80 is ruptured (not shown).

A membrane 180 of a fan-folded elastic sheet material may be included that joins the spaced apart side edges 60 of the body 10 (FIG. 2). The membrane 80 has a plurality of folds 190 aligned in parallel with the side edges 60, thereby accommodating change in the space between the side edges 60. Alternatively, in place of the membrane 80 a row of equally spaced bands made from a similar material could be used (not shown).

Figure 4:
FIG. 4 is a partial right-side elevational view of the invention, illustrating the body formed into an arcuate shape.
Figure 5:
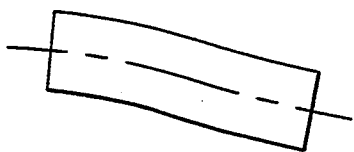
FIG. 5 is a partial right-side elevational view of the invention, illustrating the body formed into a linear shape.
Figure 6:
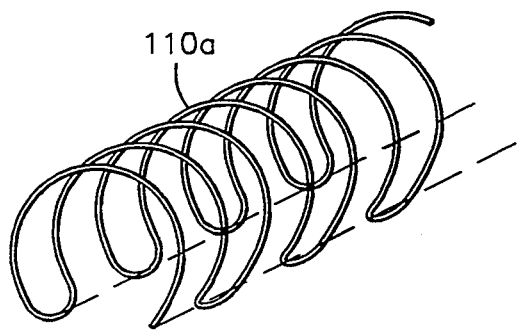
FIG. 6 is a partial perspective view of the invention, showing one embodiment of the spring-like ribs.
Figure 7:
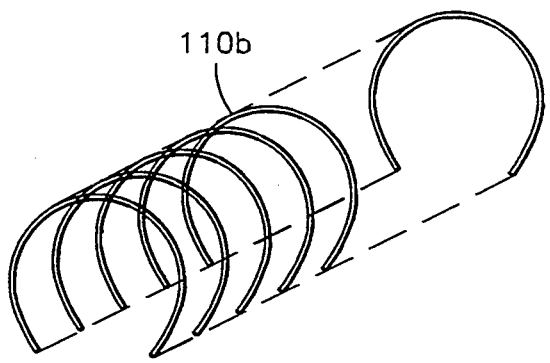
FIG. 7 is a partial perspective view of the invention, showing an alternate embodiment of the spring-like ribs.
Figure 8:
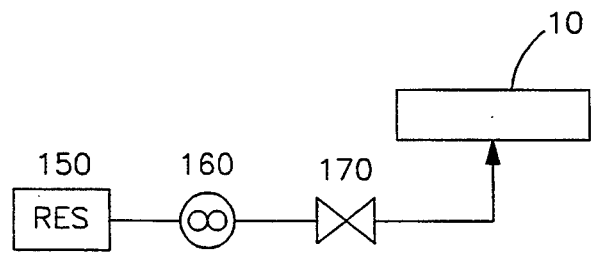
FIGS. 8 is a schematic diagram of the invention, illustrating the fluid interconnections in an embodiment including a fluid reservoir, a fluid pump, and a valve means.

The inner sheet member 90 has embedded therein a series of spaced apart, spring-like ribs 110 (FIGS. 6 and 7), which maintain the partial cylindrical shape of the body 10 while permitting the body 10 to flex between linear and arcuate shapes (FIGS. 4 and 5). The spring-like ribs 110 are preferably about 1 mm in diameter, and made of nylon or similar biologically inert material. Such spring-like ribs 110 may each be separate, as illustrated in FIG. 7, or part of a continuous spring member such as shown in FIG. 6. The continuous spring member shown in FIG. 6 has the advantage that a longitudinal biasing spring constant can be established within the inner sheet member 90 in order to partially counteract the opposing longitudinal spring constant naturally resident in the elastic inner sheet member 90. Such a spring constant in the continuous spring member may be preset to any desirable force between implantation of the device.

The first and second edge edges 40,50 may be provided with suture tabs (not shown) or other means of anchoring the end edges to the shaft 20 of the penis. Such suture tabs are preferably fixed to the device at the four intersections of the side edges 60 with the first and second end edges 40,50.

A pressurizing means 120 delivers a fluid 130 to the body 10 between the outer and inner sheet members 80,90 for expanding the outer sheet 80. The pressurizing means 120 preferably includes a receiver 130 of puncture-self-sealing material interconnected with the body 10 by a tube 140. The tube 140 is in fluid communication with both the receiver 130 and the body 10. As such, fluid may be forced into, or out of, the body 10 by injection through the receiver 130. Alteratively, the pressurizing means 130 may include a fluid reservoir 150, a fluid pump 160, and a valve means 170 for controlling the flow of fluid, of the type shown in the above prior art of Yachia et al. and Finney, each interconnected, so as to provide pumping of the fluid 130 from the fluid reservoir 150 to the body 10. The fluid 130 is restricted to flow between the sheet members 80,90. The ribs 110 provide rigidizing of the inner sheet 90 for maintaining the partial cylindrical shape and preventing collapse thereof.

In use, pressurizing of the closed sack 100 by the fluid 130 causes the outer sheet 80 to expand diametrically for enhancing the girth and length of the penis. However, insignificant force is directed inwardly towards the shaft 20 of the penis when the sack 100 is inflated due to the thickness and relative inelasticity of the inner sheet member 90, and the spring-like ribs 110 therewithin. Preferably, the device may expand to a length of about 4 inches when inflated. When deflated the device preferably has a natural length of about 2 inches.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. An implant device for expanding penile girth comprising:
   a soft, flexible body for implanting about a penile shaft beneath a penile skin between the shaft and the skin, the body formed into a shape of an elongated partial cylinder, first and second end edges defining a length of the body, and spaced apart side edges defining a circumferential limits of the cylinder and defining a space therebetween, and including an outer, relatively elastic sheet member of stretchable material, joined along the side and end edges to an inner, relatively inelastic sheet member, to form a principally closed sack, the inner sheet member having embedded therein, a series of spaced apart, spring-like ribs, the ribs maintaining the partial cylindrical shape of the body while permitting the body to flex, between linear and arcuate shapes; and
   a pressurizing means for delivering a fluid to the body between the outer and inner sheet members for expanding the outer sheet, the fluid being restricted to flow therebetween, the ribs providing rigidizing of the inner sheet for maintaining the partial cylindrical shape;
   whereby pressurizing of the closed sack by the fluid causes the outer sheet to expand diametrically to enhance the girth of the penile skin.

2. The device of claim 1 wherein the device is formed of a physiologically acceptable implant material.

3. The device of claim 2 wherein the pressurizing means includes a receiver of puncture-self-sealing material interconnected with the body by a tube, the tube being in fluid communication with both the receiver and the body, whereby the fluid may be forced into, or out of, the body by injection through the receiver.

4. The device of claim 2 wherein the pressurizing means includes a fluid reservoir, a fluid pump, and a valve means for controlling flow of the fluid interconnected to provide pumping of the fluid from the fluid reservoir to the body.

5. The device of claim 2 wherein the body has an average length of about 100 mm and a width sufficient to cover a corpus cavernosum of a penis without covering a urethra.

6. The device of claim 2 further including a membrane of fan-folded elastic sheet material joining the spaced apart side edges of the body, the fan-folded material having a plurality of folds aligned in parallel with the side edges, thereby accommodating change in the space between the side edges.

7. The device of claim 2 further including a membrane of elastic sheet material joining the spaced apart side edges of the body, the membrane being of such softness and elasticity as to expand and contract as required by movement of the spaced apart side edges of the body without pressing on a urethra.

8. An implant device for expanding penile girth comprising:
- a soft, flexible body for implanting about a penile shaft beneath a penile skin between the shaft and a skin, the body formed into a shape of an elongated partial cylinder, first and second end edges defining a length of the body, said length adapted to extend from a glans penis to the base of a penis, and spaced apart side edges defining a circumferential limits of the cylinder, and defining a space therebetween, and including an outer, relatively elastic sheet member of stretchable material, joined along the side and end edges to an inner, relatively inelastic sheet member to form a principally closed sack, the inner sheet member having embedded therein, a series of spaced apart, spring-like ribs, the ribs maintaining the partial cylindrical shape of the body while permitting the body to flex, between linear and arcuate shapes; and
- a pressurizing means for delivering a fluid to the body between the outer and inner sheet members for expanding the outer sheet, the fluid being restricted to flow therebetween, the ribs providing rigidizing of the inner sheet for maintaining the partial cylindrical shape;
- whereby pressurizing of the closed sack with the fluid causes the outer sheet to expand diametrically to enhance the girth of the penile skin.

9. The device of claim 8 wherein the device is formed of a physiologically acceptable implant material.

10. The device of claim 9 wherein the pressurizing means includes a receiver of puncture-self-sealing material interconnected with the body by a tube, the tube being in fluid communication with both the receiver and the body, whereby the fluid may be forced into, or out of, the body by injection through the receiver.

11. The device of claim 9 wherein the pressurizing means includes a fluid reservoir, a fluid pump, and a valve means for controlling flow of the fluid interconnected to provide pumping of the fluid from the fluid reservoir to the body.

12. The device of claim 9 wherein the body has an average length of about 100 mm and a width sufficient to cover a corpus cavernosum of a penis without covering a urethra.

13. The device of claim 9 further including a membrane of fan-folded elastic sheet material joining the spaced apart side edges of the body, the material having a plurality of folds aligned in parallel with the side edges, thereby accommodating changes in the space between the side edges.

14. The device of claim 9 further including a membrane of elastic sheet material joining the spaced apart side edges of the body, the membrane being of such softness and elasticity as to expand and contract as required by movement of the spaced apart side edges of the body without pressing on a urethra.

* * * * *